(12) United States Patent
Choi et al.

(10) Patent No.: US 11,046,624 B1
(45) Date of Patent: Jun. 29, 2021

(54) PRODUCTION OF LINEAR ALPHA OLEFINS FROM ORGANIC SULFIDES

(71) Applicant: SAUDI ARABIAN OIL COMPANY, Dhahran (SA)

(72) Inventors: Ki-Hyouk Choi, Dhahran (SA); Muneef F. Alqarzouh, Dhahran (SA); Abdullah T. Alabdulhadi, Dhahran (SA); Maddala V. Bhanumurthy, Yanbu (SA)

(73) Assignee: Saudi Arabian Oil Company, Dhahran (SA)

( * ) Notice: Subject to any disclaimer, the term of this patent is extended or adjusted under 35 U.S.C. 154(b) by 33 days.

(21) Appl. No.: 16/713,987

(22) Filed: Dec. 13, 2019

(51) Int. Cl.
| | |
|---|---|
| C07C 1/32 | (2006.01) |
| C07C 7/04 | (2006.01) |
| B01J 14/00 | (2006.01) |
| B01D 17/02 | (2006.01) |
| B01D 19/00 | (2006.01) |
| B01D 3/14 | (2006.01) |
| B01J 19/00 | (2006.01) |
| C10G 49/22 | (2006.01) |
| C10G 49/26 | (2006.01) |

(Continued)

(52) U.S. Cl.
CPC .............. C07C 1/322 (2013.01); B01D 3/143 (2013.01); B01D 17/02 (2013.01); B01D 19/00 (2013.01); B01J 14/00 (2013.01); B01J 19/0013 (2013.01); C07C 7/04 (2013.01); B01D 11/0403 (2013.01); B01J 2219/00087 (2013.01); C10G 31/08 (2013.01); C10G 45/26 (2013.01); C10G 47/22 (2013.01); C10G 49/007 (2013.01); C10G 49/22 (2013.01); C10G 49/26 (2013.01); C10G 2300/805 (2013.01); C10L 2290/146 (2013.01)

(58) Field of Classification Search
None
See application file for complete search history.

(56) References Cited

U.S. PATENT DOCUMENTS

| 2,390,099 A | 12/1945 | Harmen et al. |
| 2,443,852 A | 6/1948 | Eaton et al. |

(Continued)

OTHER PUBLICATIONS

Arai, et al., Hydrogenation of Hydrocarbons through Partial Oxidation in Supercritical Water, Ind. Eng. Chem. Res. 2000, 39, 4697-4701.

(Continued)

*Primary Examiner* — Ali Z Fadhel
(74) *Attorney, Agent, or Firm* — Bracewell LLP; Constance G. Rhebergen

(57) ABSTRACT

Embodiments of the disclosure provide a system and method for producing a linear alpha olefin. A disulfide, a hydrogen donating compound, and water are combined to produce a mixture. The mixture is introduced to a reactor operated at a pressure equal to or greater than 22.06 MPa and a temperature equal to or greater than 374 deg. C. to produce an effluent stream. The effluent stream is separated to produce a product stream including the linear alpha olefin. The disulfide can be a compound of formula R—S—S—R' where R is a first alkyl group having carbon atoms ranging from 1 to 12 and R' is a second alkyl group having carbon atoms ranging from 5 to 12. The hydrogen donating compound can include a partially hydrogenated multi-ring aromatic compound.

21 Claims, 3 Drawing Sheets

(51) Int. Cl.
*C10G 49/00* (2006.01)
*C10G 45/26* (2006.01)
*C10G 31/08* (2006.01)
*C10G 47/22* (2006.01)
*B01D 11/04* (2006.01)

(56) References Cited

U.S. PATENT DOCUMENTS

| | | | |
|---|---|---|---|
| 2,468,739 | A | 5/1949 | Eaton et al. |
| 3,419,614 | A | 12/1968 | Doss et al. |
| 4,119,549 | A | 10/1978 | Davis |
| 8,535,518 | B2 | 9/2013 | Choi et al. |
| 9,005,432 | B2 | 4/2015 | Choi et al. |
| 9,039,889 | B2 | 5/2015 | Choi et al. |
| 9,663,461 | B2 | 5/2017 | Cazaux et al. |
| 2003/0010677 | A1 | 1/2003 | Schinski |
| 2012/0061291 | A1* | 3/2012 | Choi ............ C10G 49/22 208/53 |
| 2015/0218465 | A1 | 8/2015 | Choi et al. |
| 2016/0312129 | A1* | 10/2016 | Choi ............ C10G 49/18 |
| 2019/0264110 | A1 | 8/2019 | Choi et al. |
| 2019/0270642 | A1* | 9/2019 | Leroi ............ C07C 1/322 |

OTHER PUBLICATIONS

Coope, et al., The Thermal Decomposition of Dimethyl Disulphide, Canadian Journal of Chemistry. vol. 32, pp. 768-779.

Escobar, et al., Naphthalene hydrogenation over Mg-doped Pt/Al2O3, Catalysis Today, vol. 296, pp. 197-204 (2017).

Gagnon et al., Thermal Decomposition of 1-Hexanethiol, Can. J. Chem. vol. 37, pp. 1846-1850, 1959.

Hurst, et al., Polycyclic Aromatic Hydrocarbons Formation and Growth during the Supercritical Pyrolysis of 1-Octene, Proceedings of the Combustion Institute, in press (2018).

Industrial Organic Chemistry, 1993, pp. 73-79, ISBN 0-89573-861-9.

Katritzky, et al., Aqueous High-Temperature Chemistry of Carbo- and Hetrocycles. 16. Model Sulfur Compounds: A Study of Hydrogen Sulfide Generation, Energy&Fuels, vol. 5 No. 6, 1991, 823-834.

Katritzky, et al., Reactions in High-Temperature Aqueous Media, Chemical Reviews, 2001, vol. 101, No. 4, 837-892.

Kida, et al., Combining Experiment and Theory to Elucidate the Role of Supercritical Water in Sulfide Decomposition, Phys. Chem. Chem. Phys., 2014, 16, 9220-9228.

Lappin, Routes to Alpha Olefins, Alpha Olefins Applications Handbook, 1989 pp. 56-58. ISBN 978-0824778958.

Matsuo, et al., Mild Preparation of Alkenes from Phenyl Sulfides: One-Pot Elimination of Phenylthio Group via Sulfilimine at Ambient Temperature, Organic Letters, vol. 8, No. 26, 2006, 6095-6098.

Patwardhan, et al., Supercritical Water Desulfurization of Organic Sulfides is Consistent with Free-Radical Kinetics, Energy & Fuels, Energy Fuels, 2013, 27 (10), pp. 6108-6117.

Siskin, et al., Reactivity of Organic Compounds in Superheated Water: General Background, Chemical Reviews, 2001, vol. 101, No. 4. 823-835.

Yang, et al., A study of thermal decomposition of alkanethiols in pressure reactor, Fuel Processing technol., vol. 87, pp. 673-678, 2006.

PCT International Search Report issued for PCT/US2020/064660, dated Mar. 15, 2021, 57 pages.

* cited by examiner

PRODUCTION OF LINEAR ALPHA OLEFINS FROM ORGANIC SULFIDES

BACKGROUND

Field of the Disclosure

Embodiments of the disclosure generally relate to producing linear alpha olefins. More specifically, embodiments of the disclosure relate to a method and system for producing linear alpha olefins using organic sulfide compounds and supercritical water.

Description of the Related Art

Linear alpha olefins (LAOs) are aliphatic hydrocarbons having a carbon-carbon double bond in the terminal position. LAOs are typically used as raw materials for products such as linear low density polyethylene (LLDPE), surfactants, and synthetic lubricant oils. In an industrial scale, LAOs are produced by methods such as catalytic oligomerization of ethylene, catalytic dehydrogenation of n-paraffins, and thermal cracking of n-paraffins.

In a Ziegler process, LAOs are produced by using ethylene as a feed material in the presence of an organometallic catalyst. In a Pacol process, olefins are produced by converting C6 to C19 n-paraffins in the presence of a heterogeneous catalyst. The produced olefins are a mixture of internal olefins and LAOs. In a thermal cracking process, C20 to C30 n-paraffins (generally in the form of wax) are used as a feed material and are subjected to a temperature ranging between 500 deg. C. and 600 deg. C. in the presence of steam at ambient or marginally elevated pressure. The residence time in the thermal cracking reactor ranges between 7 to 15 seconds, where the conversion rate is about 25%, in which 90% to 95% are LAOs.

Due to the complexities of separating internal olefins, branched olefins, and LAOs from a produced mixture, it is necessary for LAO production processes to be selective in producing LAOs as opposed to internal olefins and branched olefins. Although there are certain separation schemes proposed and implemented in industrial scale, the purity of the LAO-containing product is still a key consideration for successfully producing LAOs.

SUMMARY

Embodiments of the disclosure generally relate to producing linear alpha olefins. More specifically, embodiments of the disclosure relate to a method and system for producing linear alpha olefins using organic sulfide compounds and supercritical water.

Embodiments of the disclosure provide a method for producing an LAO. The method includes the step of combining a disulfide oil feed and a hydrogen donor feed to produce a first mixed stream. The disulfide oil feed includes a disulfide. The hydrogen donor feed includes a hydrogen donating compound (HDC). The method includes the step of combining the first mixed stream and a water feed to produce a second mixed stream. The method includes the step of introducing the second mixed stream to a reactor. The reactor is operated at a pressure equal to or greater than 22.06 MPa and a temperature equal to or greater than 373.9 deg. C. to produce an effluent stream. The effluent stream includes the LAO. The method includes the step of introducing the effluent stream to a first separator to produce a gas stream and a liquid stream. The liquid stream includes the LAO. The method includes the step of introducing the liquid stream to a second separator to produce a hydrocarbon stream and a water stream. The hydrocarbon stream includes the LAO. The method includes the step of introducing the hydrocarbon stream to a distillation unit to produce an LAO stream and a byproduct stream. The LAO stream includes the LAO.

In some embodiments, the method further includes the step of pressurizing the first mixed stream to a pressure equal to or greater than 22.06 MPa. In some embodiments, the method further includes the step of heating the first mixed stream to a temperature ranging between 80 deg. C. and 150 deg. C. In some embodiments, the method further includes the step of pressurizing the water feed to a pressure equal to or greater than 22.06 MPa. In some embodiments, the method further includes the step of heating the water feed to a temperature ranging between 374 deg. C. and 500 deg. C. In some embodiments, the method further includes the step of cooling the effluent stream to a temperature ranging between 50 deg. C. and about 110 deg. C. In some embodiments, the method further includes the step of depressurizing the effluent stream to ambient pressure.

In some embodiments, the disulfide is a compound of formula R—S—S—R' where R is a first alkyl group having carbon atoms ranging from 1 to 12 and R' is a second alkyl group having carbon atoms ranging from 5 to 12. In some embodiments, the disulfide includes 1-(pentyldisulfanyl)pentane.

In some embodiments, The HDC includes a partially hydrogenated multi-ring aromatic compound. In some embodiments, the HDC includes 1,2,3,4-tetrahydronaphthalene, 6-butyl-1,2,3,4-tetrahydronaphthalene, 7-ethyl-1,2,3,4-tetrahydronaphthalene, 9,10-dihydroanthracene, 9,10-dihydrophenanthrene, and combinations of the same.

In some embodiments, the first mixed stream has an HDC-to-disulfide mole ratio ranging between 0.1:1 and 0.5:1. In some embodiments, the second mixed stream has an oil-to-water volume ratio ranging between 0.5:1 and 0.2:1 at standard temperature and pressure.

In some embodiments, the byproduct stream includes a dehydrogenated form of the HDC including naphthalene, 1,2-dihydronaphthalene, anthracene, phenanthrene, and combinations of the same. In some embodiments, the method further includes the step of regenerating the dehydrogenated form of the HDC.

Embodiments of the disclosure also provide a method for producing an LAO. The method includes the step of combining a disulfide, an HDC, and water to produce a mixture. The method includes the step of pressurizing the mixture to a pressure equal to or greater than 22.06 MPa and heating the mixture to a temperature equal to or greater than 374 deg. C. The disulfide is a compound of formula R—S—S—R' where R is a first alkyl group having carbon atoms ranging from 1 to 12 and R' is a second alkyl group having carbon atoms ranging from 5 to 12. The HDC includes a partially hydrogenated multi-ring aromatic compound.

In some embodiments, the disulfide includes 1-(pentyldisulfanyl)pentane. In some embodiments, the HDC includes 1,2,3,4-tetrahydronaphthalene, 6-butyl-1,2,3,4-tetrahydronaphthalene, 7-ethyl-1,2,3,4-tetrahydronaphthalene, 9,10-dihydroanthracene, 9,10-dihydrophenanthrene, and combinations of the same.

Embodiments of the disclosure also provide a system for producing an LAO. The system includes a first mixer, a first pump, a first heat exchanger, a second pump, a second heat exchanger, a second mixer, a reactor, a third heat exchanger, a pressure reducer, a first separator, a second separator, and a distillation unit. The first mixer is configured to combine a disulfide oil feed and a hydrogen donor feed to produce a first mixed stream. The disulfide oil feed includes a disulfide. The hydrogen donor feed includes an HDC. The first pump is fluidly connected downstream of the first mixer. The first pump is configured to pressurize the first mixed stream to a pressure equal to or greater than 22.06 MPa. The first heat exchanger is fluidly connected downstream of the first mixer. The first heat exchanger is configured to heat the first mixed stream to a temperature ranging between 80 deg. C. and 150 deg. C. The second pump is configured to pressurize a water feed to a pressure equal to or greater than 22.06 MPa. The second heat exchanger is configured to heat the water feed to a temperature ranging between 374 deg. C. and 500 deg. C. The second mixer is fluidly connected downstream of the first pump and the first heat exchanger and fluidly connected downstream of the second pump and the second heat exchanger. The second mixer is configured to combine the first mixed stream and the water feed to produce a second mixed stream. The reactor is fluidly connected downstream of the second mixer. The reactor is operated at a pressure equal to or greater than 22.06 MPa and a temperature equal to or greater than 373.9 deg. C. to produce an effluent stream. The effluent stream includes the LAO. The third heat exchanger is fluidly connected downstream of the reactor. The third heat exchanger is configured to cool the effluent stream to a temperature ranging between 50 deg. C. and about 110 deg. C. The pressure reducer is fluidly connected downstream of the reactor. The pressure reducer is configured to depressurize the effluent stream to ambient pressure. The first separator is fluidly connected downstream of the third heat exchanger and the pressure reducer. The first separator is configured to separate the effluent stream into a gas stream and a liquid stream. The liquid stream includes the LAO. The second separator is fluidly connected downstream of the first separator. The second separator is configured to separate the liquid stream into a hydrocarbon stream and a water stream. The hydrocarbon stream includes the LAO. The distillation unit is fluidly connected downstream of the second separator. The distillation unit is configured to separate the hydrocarbon stream to produce an LAO stream and a byproduct stream. The LAO stream includes the LAO.

In some embodiments, the system further includes a Merox unit. The Merox unit is fluidly connected upstream of the first mixer. The Merox unit is configured to produce the disulfide oil feed by removing sulfur from naphtha and kerosene.

BRIEF DESCRIPTION OF THE DRAWINGS

So that the manner in which the previously-recited features, aspects, and advantages of the embodiments of this disclosure as well as others that will become apparent are attained and can be understood in detail, a more particular description of the disclosure briefly summarized previously may be had by reference to the embodiments that are illustrated in the drawings that form a part of this specification. However, it is to be noted that the appended drawings illustrate only certain embodiments of the disclosure and are not to be considered limiting of the disclosure's scope as the disclosure may admit to other equally effective embodiments.

Figure 1:
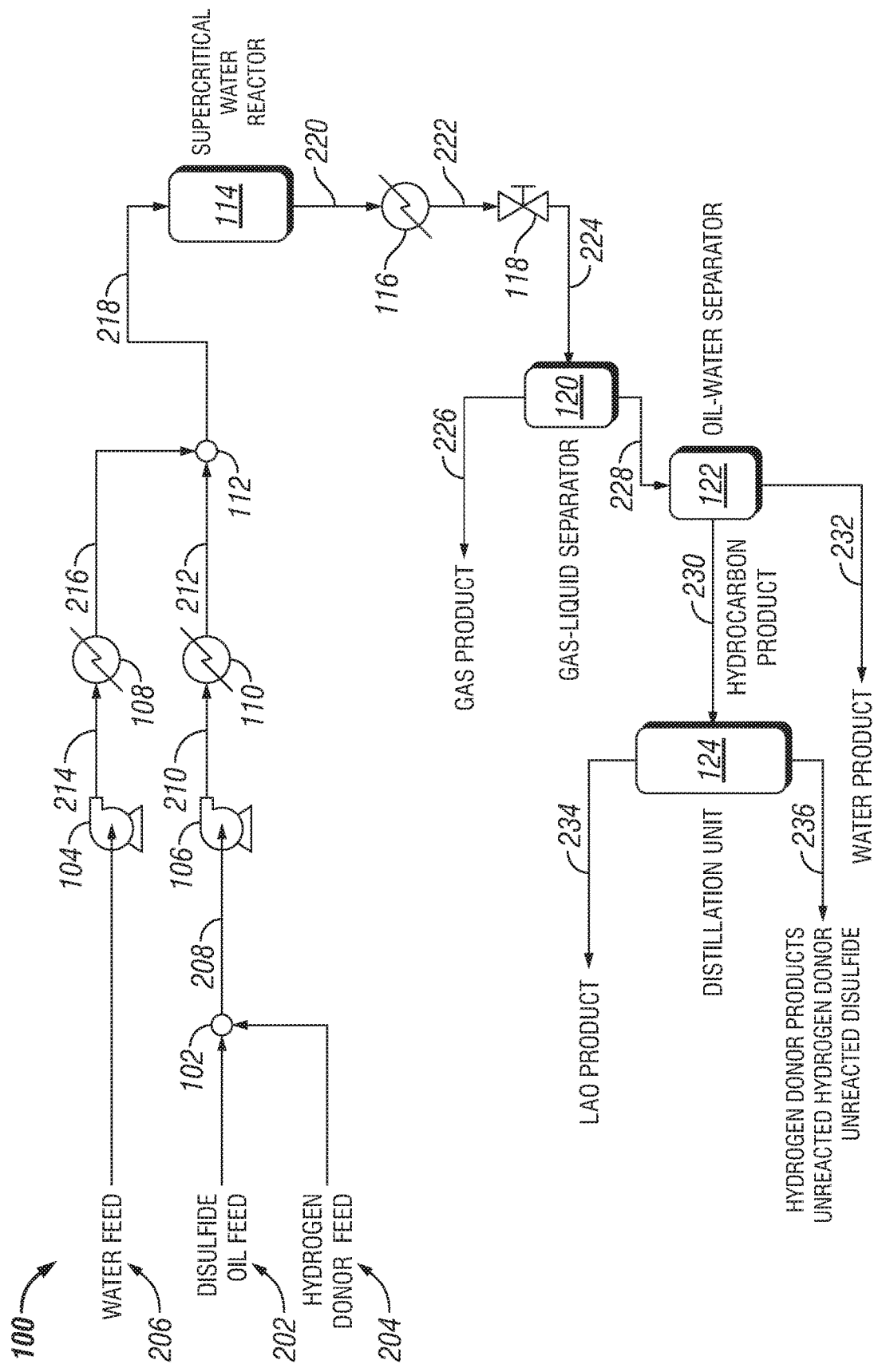
FIG. 1 is a schematic diagram of a process for LAO production according to an embodiment of the disclosure.

In the accompanying Figures, similar components or features, or both, may have a similar reference label.

DETAILED DESCRIPTION

The disclosure refers to particular features, including process or method steps and systems. Those of skill in the art understand that the disclosure is not limited to or by the description of embodiments given in the specification. The subject matter of this disclosure is not restricted except only in the spirit of the specification and appended claims.

Those of skill in the art also understand that the terminology used for describing particular embodiments does not limit the scope or breadth of the embodiments of the disclosure. In interpreting the specification and appended claims, all terms should be interpreted in the broadest possible manner consistent with the context of each term. All technical and scientific terms used in the specification and appended claims have the same meaning as commonly understood by one of ordinary skill in the art to which this disclosure belongs unless defined otherwise.

Although the disclosure has been described with respect to certain features, it should be understood that the features and embodiments of the features can be combined with other features and embodiments of those features.

Although the disclosure has been described in detail, it should be understood that various changes, substitutions, and alternations can be made without departing from the principle and scope of the disclosure. Accordingly, the scope of the present disclosure should be determined by the following claims and their appropriate legal equivalents.

As used throughout the disclosure, the singular forms "a," "an," and "the" include plural references unless the context clearly indicates otherwise.

As used throughout the disclosure, the word "about" includes +/−5% of the cited magnitude. The word "substantially" includes +/−5% of the cited magnitude.

As used throughout the disclosure, the words "comprise," "has," "includes," and all other grammatical variations are each intended to have an open, non-limiting meaning that does not exclude additional elements, components or steps. Embodiments of the present disclosure may suitably "comprise," "consist," or "consist essentially of" the limiting features disclosed, and may be practiced in the absence of a limiting feature not disclosed. For example, it can be recognized by those skilled in the art that certain steps can be combined into a single step.

As used throughout the disclosure, the words "optional" or "optionally" means that the subsequently described event or circumstances can or may not occur. The description includes instances where the event or circumstance occurs and instances where it does not occur.

Where a range of values is provided in the specification or in the appended claims, it is understood that the interval encompasses each intervening value between the upper limit and the lower limit as well as the upper limit and the lower limit. The disclosure encompasses and bounds smaller ranges of the interval subject to any specific exclusion provided.

Where reference is made in the specification and appended claims to a method comprising two or more defined steps, the defined steps can be carried out in any order or simultaneously except where the context excludes that possibility.

As used throughout the disclosure, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present disclosure.

As used throughout the disclosure, spatial terms described the relative position of an object or a group of objects relative to another object or group of objects. The spatial relationships apply along vertical and horizontal axes. Orientation and relational words such are for descriptive convenience and are not limiting unless otherwise indicated.

As used throughout the disclosure, the term "external supply of hydrogen" refers to the addition of hydrogen to the feed to the reactor or to the reactor itself. For example, a reactor in the absence of an external supply of hydrogen means that the feed to the reactor and the reactor are in the absence of added hydrogen such that no hydrogen is a feed or a part of a feed to the reactor.

As used throughout the disclosure, the term "external supply of catalyst" refers to the addition of catalyst to the feed to the reactor or the presence of a catalyst in the reactor, such as a fixed bed catalyst in the reactor. For example, a reactor in the absence of an external supply of catalyst means no catalyst has been added to the feed to the reactor and the reactor does not contain a catalyst bed in the reactor.

As used throughout the disclosure, the terms "mercaptan" or "thiol" refer to a compound with a carbon-sulfur bond in the form R—SH, where R can have a carbon number of 1 for a mercaptan (in the form $CH_3SH$) and R can have a carbon number between 2 and 12.

As used throughout the disclosure, the terms "disulfide" or "disulfide compound" refer to aliphatic, organic, sulfur-containing compounds taking the form R—S—S—R', where each of R and R' can have a carbon number between 1 and 12.

Embodiments of the disclosure provide processes and systems of an LAO producing process using aliphatic sulfur compounds such as disulfides in the presence of supercritical water. Hydrogen donating compounds are used to suppress and prevent secondary reactions of LAOs.

It is known in the art that supercritical water has unique properties making it suitable for use as a petroleum reaction medium where the reaction objectives can include conversion reactions, desulfurization reactions, denitrogenation reactions, and demetallization reactions. Supercritical water is water at a temperature at or greater than the critical temperature of water and at a pressure at or greater than the critical pressure of water. The critical temperature of water is 373.946 deg. C. The critical pressure of water is 22.06 megapascals (MPa). Advantageously, at supercritical conditions water acts as both a hydrogen source and a solvent (diluent) in conversion reactions, desulfurization reactions and demetallization reactions and a catalyst is not needed. Hydrogen from the water molecules is transferred to the hydrocarbons through direct transfer or through indirect transfer, such as the water gas shift reaction.

Without being bound any theory, it is understood that the basic reaction mechanism of supercritical water mediated petroleum processes is similar to a free radical reaction mechanism. Radical reactions include initiation, propagation, and termination steps. With hydrocarbons, initiation is the most difficult step. Initiation requires the breaking of chemical bonds. The bond energy of carbon-carbon bonds (C—C) is about 350 kilojoules per mole (kJ/mol), while the bond energy of carbon-hydrogen bonds (C—H) is about 420 kJ/mol, both of which are considered high chemical bond energies. Due to the high chemical bond energies, carbon-carbon bonds and carbon-hydrogen bonds do not break easily at the temperatures in a supercritical water process, 380 deg. C. to 450 deg. C., without catalyst or radical initiators. In contrast, carbon-sulfur bonds (C—S) have a bond energy of about 250 kJ/mol. Aliphatic carbon-sulfur bonds, such as included in thiols, sulfides, and disulfides, have a lower bond energy than the aromatic carbon-sulfur bond. In addition, aliphatic sulfur-sulfur bonds (S—S), such as included in disulfides, have a bond energy lesser than that of carbon-sulfur bonds. For comparison, n-heptane has a C1-C2 dissociation energy of about 368.2 kJ/mol. Butane-1-thiol has a C—S dissociation energy of about 309 kJ/mol. (Methyldisulfanyl)methane (or dimethyl disulfide) has a S—S dissociation energy of about 272 kJ/mol. Although aliphatic sulfur compounds generally have lesser bond dissociation energy than aliphatic hydrocarbons, it is known that disulfides and thiol compounds are not readily decomposed at a temperature lesser than 350 deg. C. For example, dimethyl disulfide has an induction period of about 120 seconds at about 314 deg. C. to be decomposed. At about 360 deg. C., the induction period is reduced to about 35 seconds. The main decomposition product of dimethyl disulfide is methanethiol (or methyl mercaptan). Another example includes 1-hexanethiol (or hexyl mercaptan), where the conversion rate is about 10% at about 350 deg. C. producing olefinic compounds.

Thermal energy creates radicals through chemical bond breakage. Supercritical water creates a "cage effect" by surrounding the radicals. The radicals surrounded by water molecules cannot react easily with each other, and thus, intermolecular reactions that contribute to coke formation are suppressed. The cage effect suppresses coke formation by limiting inter-radical reactions. Supercritical water, having low dielectric constant, dissolves hydrocarbons and surrounds radicals to prevent the inter-radical reaction, which is the termination reaction resulting in condensation (dimerization or polymerization). Because of the barrier set by the supercritical water cage, hydrocarbon radical transfer is more difficult in supercritical water as compared to conventional thermal cracking processes, such as delayed coker, where radicals travel freely without such barriers.

Sulfur compounds released from sulfur-containing molecules can be converted to hydrogen sulfide, mercaptans, and elemental sulfur. Without being bound to a particular theory, it is believed that hydrogen sulfide is not "stopped" by the supercritical water cage due its small size and chemical structure similar to water. Hydrogen sulfide can travel freely through the supercritical water cage to propagate radicals and distribute hydrogen. Hydrogen sulfide can lose its hydrogen due to hydrogen abstraction reactions with hydrocarbon radicals. The resulting hydrogen-sulfur radical (HS.) is capable of abstracting hydrogen from hydrocarbons (including disulfides and thiyl radicals) which will result in formation of more radicals. Thus, hydrogen sulfide in radical reactions acts as a transfer agent to transfer radicals and abstract/donate hydrogen. However, without a diluent such as supercritical water, hydrogen-sulfur radicals can lead to secondary reactions of the produced LAO, such as isomerization. For example, internal olefins are more stable than terminal olefins. The carbon-carbon double bond position of terminal olefins can be rearranged via isomerization to an internal position in the presence of hydrogen-sulfur radicals resulting from hydrogen sulfide reducing the LAO yield. The presence of a catalyst may also lead to isomerization of LAOs to internal or branched olefins, even in cases when the catalyst has marginal acidity.

As previously noted, aromatic sulfur compounds are more stable in supercritical water compared to more active aliphatic sulfur compounds. As a result, a feedstock having more aliphatic sulfur can have a higher activity in supercritical water. Organic disulfides, such as diethyl disulfide, has a similar bond dissociation energy (S—S bond) as a C—S bond. Decomposition of one mole of organic disulfide can generate two moles of thiyl radicals, which means labile organic disulfide is a useful precursor for terminal olefin production in supercritical water.

Aliphatic sulfur compounds are generally found in naphtha, kerosene, and vacuum residue. In vacuum residue, aliphatic carbon-sulfur bonds are believed to be present in an asphalthenic fraction. The amount of aliphatic sulfur compounds is less than aromatic sulfur compounds in common crude oils. Thus, it is required to find an aliphatic sulfur rich stream in refinery as a reactant for producing LAOs.

FIG. 1 shows a schematic diagram of a process 100 for LAO production, according to an embodiment of the disclosure. The process 100 can include mixer 102, pump 104, pump 106, heat exchanger 108, heat exchanger 110, mixer 112, supercritical water reactor 114, heat exchanger 116, pressure reducer 118, separator 120, separator 122, and distillation unit 124.

Disulfide oil feed 202 is introduced to the process 100. Disulfide oil feed 202 can be selected from a stream containing aliphatic sulfur compounds including disulfides. Disulfide oil feed 202 can include natural gas, liquefied petroleum gas (LPG), naphtha, or kerosene. The disulfide compounds included in disulfide oil feed 202 can have boiling points ranging between about 200 deg. C. and about 400 deg. C., alternately between about 230 deg. C. and about 360 deg. C., or alternately between about 260 deg. C. and about 320 deg. C. In at least one embodiment, the disulfide compounds included in disulfide oil feed 202 have boiling points ranging between 260 deg. C. and about 320 deg. C. Disulfide oil feed 202 can include greater than about 20 wt. % of disulfide compounds having boiling points greater than about 260 deg. C., alternately greater than about 30 wt. % of disulfide compounds having boiling points greater than about 260 deg. C., or alternately greater than about 50 wt. % of disulfide compounds having boiling points greater than about 260 deg. C. In at least one embodiment, disulfide oil feed 202 includes greater than about 50 wt. % of disulfide compounds having boiling points greater than about 260 deg. C. Disulfide oil feed 202 can include disulfide compounds containing C1 to C12 groups. Disulfide oil feed 202 can include disulfide compounds containing C5 groups, C5 to C6 groups, C5 to C7 groups, C5 to C7 groups, C5 to C8 groups, C5 to C9 groups, C5 to C10 groups, C5 to C11 groups, and C5 to C12 groups. Non-limiting example disulfide compounds include 1-(pentyldisulfanyl)pentane (or dipentyl disulfide, having a boiling point of about 264 deg. C.), 1-(pentyldisulfanyl)hexane (or pentyl hexyl disulfide), 1-(hexyldisulfanyl)hexane (or dihexyl disulfide), 1-(hexyldisulfanyl)heptane (or hexyl heptyl disulfide), and 1-(heptyldisulfanyl)heptane (or diheptyl disulfide). In at least one embodiment, the disulfide oil includes dipentyl disulfide. In at least one embodiment, the disulfide oil includes a disulfide compound having at least one C5 group. Disulfide oil feed 202 can include greater than about 5 wt. % disulfide compounds, alternately greater than about 10 wt. % disulfide compounds, alternately greater than about 20 wt. % disulfide compounds. In at least one embodiment, disulfide oil feed 202 includes greater than about 20 wt. % disulfide compounds. Disulfide oil feed 202 can have a total sulfur content of greater than about 1 wt. %, alternately greater than about 3 wt. %, or alternately greater than about 5 wt. %. In at least one embodiment, disulfide oil feed 202 has a total sulfur content of greater than about 5 wt. %. The sodium content in disulfide oil feed 202 is less than about 50 parts-per-million by weight (wt. ppm), alternately less than 40 wt. ppm, alternately less than 30 wt. ppm, alternately less than 20 wt. ppm, or alternately less than 10 wt. ppm. Maintaining a sodium content in disulfide oil 12 of less than 50 wt. ppm reduces or eliminates alkali precipitation in supercritical water reactor 114. Advantageously, disulfides are more manageable to process than hydrogen sulfide, because hydrogen sulfide is difficult to compress to supercritical water conditions and can be difficult to handle. In contrast, disulfides are safely handled and can mix within the hydrocarbon stream at supercritical water conditions. In at least one embodiment, disulfide oil feed 202 can contain disulfides, trisulfides, mercaptans, alkanes, alkenes, and combinations of the same. In at least one embodiment, disulfide oil feed 202 can further contain other hydrocarbons.

In general, the most abundant form of sulfur compounds found in petroleum crude oil is thiophenic sulfur. A lesser quantity of aliphatic sulfur are concentrated in light fractions such as naphtha and kerosene. The sulfur concentration of aliphatic sulfur included in crude oil ranges between about 0.1 wt. % and about 1 wt. %.

To increase the aliphatic sulfur content for LAO production, the disulfide oil can be produced by a caustic extraction process such as a Merox process. A Merox process is a desulfurization process. In general, a Merox process can remove sulfur from natural gas, LPG, naphtha, and kerosene. Mercaptans present in a diesel fraction or heavier fraction cannot be treated by Merox because those fractions have low miscibility with caustic solutions, and thus have phase transfer limitations. The following reactions occur in a Merox unit:

$$2R-SH + 2\ NaOH \rightarrow 2\ NaS-R + 2H_2O \qquad \text{Reaction (1)}$$

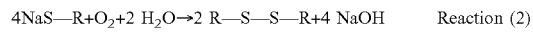
$$4NaS-R + O_2 + 2\ H_2O \rightarrow 2\ R-S-S-R + 4\ NaOH \qquad \text{Reaction (2)}$$

where R—SH represents a mercaptan or thiol (where R represents an alkyl group containing at least one carbon), NaOH is sodium hydroxide, NaS—R is a sodium bonded to an (S—R)⁻ ion, where the R is an alkyl group, H₂O is water, O₂ is oxygen, and R—S—S—R represents a disulfide.

Figure 2:
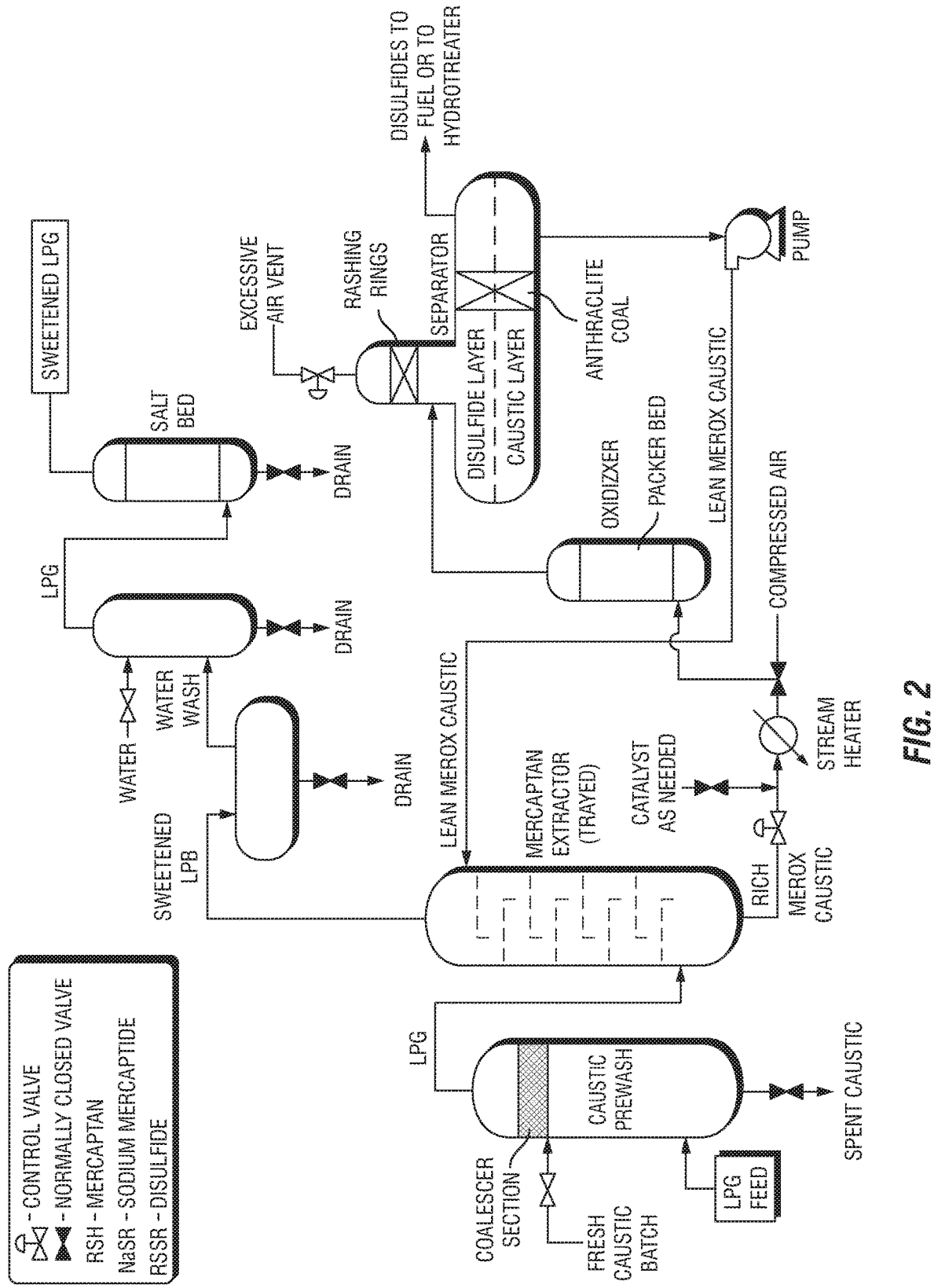
FIG. 2 is a schematic diagram of a Merox process.

In a Merox process, a caustic solution containing sodium hydroxide reacts with a thiol to form NaSR, which is extracted to a water phase. The NaSR can then be reacted with oxygen to form a water insoluble disulfide and sodium hydroxide. The sodium hydroxide can be recycled to the front of the process. The disulfide oil can be separated from the caustic solution and air by a phase separator. An embodiment of a Merox process is shown in FIG. 2.

Referring back to FIG. 1, hydrogen donor feed 204 is introduced to the process 100. Hydrogen donor feed 204 includes an HDC. The HDC is used to prevent secondary reactions of LAOs therefore enhancing the yield of LAOs. Hydrogen donor feed 204 can be selected from a residual fraction of distillate, hydrocracker, coker, visbreaker, hydrotreater, and catalytic cracker. Hydrogen donor feed 204 can also be selected from extracts of liquefied coal, petroleum refinery distillates, cracked products from a petroleum refinery product stream, and residue from a petrorefinery. The HDC included in hydrogen donor feed 204 can have a boiling point ranging between about 100 deg. C. and about 450 deg. C., alternately between about 150 deg. C. and about 400 deg. C., or alternately between about 200 deg. C. and about 350 deg. C. In at least one embodiment, the HDC included in hydrogen donor feed 204 has a boiling point ranging between about 200 deg. C. and about 350 deg. C. Advantageously, the use of HDC having a boiling point equal to or greater than about 200 deg. C. allows separation of product LAOs by distillation methods. Advantageously, the use of HDC having a boiling point equal to or less than about 350 deg. C. reduces the difficulty of mixing the HDCs with the disulfide oil and supercritical water.

Non-limiting example HDCs include partially hydrogenated multi-ring aromatic compounds such as 1,2,3,4-tetrahydronaphthalene (or tetralin, having a boiling point of about 207 deg. C.), alkylated derivatives of tetralin including 6-butyl-1,2,3,4-tetrahydronaphthalene (or 6-butyl tetralin) and 7-ethyl-1,2,3,4-tetrahydronaphthalene (or 7-ethyl tetralin), 9,10-dihydroanthracene (having a boiling point of about 312 deg. C.), alkylated derivatives of 9,10-dihydroanthracene, 9,10-dihydrophenanthrene (having a boiling point of about 308 deg. C.), and alkylated derivatives of 9,10-dihydrophenanthrene. Non-limiting example HDCs also include normal paraffinic hydrocarbons having six or greater carbon atoms such as n-eicosane (C21), n-docosane (C22), and n-octacosane (C28).

Disulfide oil feed 202 and hydrogen donor feed 204 are passed to mixer 102 to produce mixed stream 208. Mixer 102 can be any type of mixing device capable of mixing disulfide oil feed 202 and hydrogen donor feed 204. Non-limiting examples of mixing devices suitable for use as mixer 102 can include a tee junction, a static mixer, an inline mixer, and impeller-embedded mixer. Mixed stream 208 can have an HDC-to-disulfide mole ratio ranging between about 0.01:1 and about 2:1, alternately between about 0.05:1 and about 1:1, or alternately between about 0.1:1 and about 0.5:1. In at least one embodiment, mixed stream 208 has an HDC-to-disulfide mole ratio is about 0.2:1.

The mole quantity of HDCs included in hydrogen donor feed 204 can be determined by the mole quantity of disulfide compounds included in the disulfide oil feed 202 to produce mixed stream 208. Without being bound by any theory, one mole of tetralin can donate four moles of hydrogen atoms for LAO production and convert to one mole of naphthalene (having a boiling point of about 218 deg. C.). One mole of 9,10-dihydroanthracene or 9,10-dihydrophenanthrene can donate two moles of hydrogen atoms for LAO production and convert to one mole of anthracene or phenanthrene, respectively. One mole of disulfide compound requires two moles of hydrogen atoms from the HDC to produce two moles of LAO molecules. Although the HDC-to-disulfide mole ratio accordingly ranges between about 0.5:1 and about 1:1, the mole ratio can be adjusted to a range between about 0.1:1 and about 0.5:1 to prevent undesirable reactions between the HDC, the LAO, and the disulfide compounds.

Mixed stream 208 can be passed to pump 106. Pump 106 can be any type of pump capable of increasing the pressure of mixed stream 208. In at least one embodiment, pump 106 is a diaphragm metering pump. The pressure of mixed stream 208 can be increased in pump 106 to produce mixed stream 210. The pressure of mixed stream 210 can be greater than about 22 MPa. In at least one embodiment, the pressure of mixed stream 210 is greater than about 22.06 MPa, which is greater than the critical pressure of water.

Mixed stream 210 can be passed to heat exchanger 110. Heat exchanger 110 can be any type of heat exchanger capable increasing the temperature of mixed stream 210. Non-limiting examples of heat exchanger 110 can include an electric heater, a fired heater, and a cross exchanger. The temperature of mixed stream 210 can be increased in heat exchanger 110 to produce mixed stream 212. The temperature of mixed stream 212 can range between about room temperature and about 250 deg. C., alternately between about 50 deg. C. and about 200 deg. C., or alternately between about 80 deg. C. and about 150 deg. C. In at least one embodiment, the temperature of mixed stream 212 ranges between about 80 deg. C. and about 150 deg. C.

Water feed 206 is introduced to the process 100. Water feed 206 can be a demineralized water. Water feed 206 can have a conductivity less than about 1.0 microSiemens per centimeter (0/cm), alternately less than about 0.5 µS/cm, or alternately less than about 0.1 µS/cm. In at least one embodiment, water feed 206 has a conductivity less than about 0.1 µS/cm. Water feed 206 can have a sodium content less than about 10 micrograms per liter (µg/L), alternately less than about 5 µg/L, or alternately less than about 1 µg/L. In at least one embodiment, water feed 206 has a sodium content less than about 1 µg/L. Water feed 206 can have a chloride content less than about 5 µg/L, alternately less than about 3 µg/L, or alternately less than about 1 µg/L. In at least one embodiment, water feed 206 has a chloride content less than about 1 µg/L. Water feed 206 can have a silica content less than about 5 µg/L, alternately less than about 4 µg/L, or alternately less than about 3 µg/L. In at least one embodiment, water feed 206 has a silica content less than about 3 µg/L.

Water feed 206 can be passed to pump 104. Pump 104 can be any type of pump capable of increasing the pressure of water feed 206. In at least one embodiment, pump 104 is a diaphragm metering pump. The pressure of water feed 206 can be increased in pump 104 to produce water stream 214. The pressure of water stream 214 can be greater than about 22 MPa. In at least one embodiment, the pressure of water stream 214 is greater than about 22.06 MPa, which is greater than the critical pressure of water.

Water stream 214 can be passed to heat exchanger 108. Heat exchanger 108 can be any type of heat exchanger capable increasing the temperature of water stream 214. Non-limiting examples of heat exchanger 108 can include an electric heater, a fired heater, and a cross exchanger. The temperature of water stream 214 can be increased in heat exchanger 108 to produce water stream 216. The temperature of water stream 216 can range between about 200 deg. C. and about 600 deg. C., alternately between about 300 deg. C. and about 550 deg. C., or alternately between about 350 deg. C. and about 500 deg. C. In at least one embodiment, the temperature of water stream 216 ranges between about 374 deg. C. and about 500 deg. C., which is greater than the critical temperature of water.

In some embodiments, disulfide oil feed 202, hydrogen donor feed 204, and water feed 206 can each separately be pressurized to a pressure of greater than about 22 MPa, alternately between about 23 MPa and about 30 MPa, or alternately between about 24 MPa and about 26 MPa.

In some embodiments, disulfide oil feed 202, hydrogen donor feed 204, and water feed 206 can each separately be heated to a temperature ranging between about 200 deg. C. and about 600 deg. C., alternately between about 300 deg. C. and about 550 deg. C., or alternately between about 350 deg. C. and about 500 deg. C.

Mixed stream 212 and water stream 216 are passed to mixer 112 to produce mixed stream 218. Mixer 112 can be any type of mixing device capable of mixing mixed stream 212 and water stream 216. Non-limiting examples of mixing devices suitable for use as mixer 112 can include a tee junction, a static mixer, an inline mixer, and impeller-embedded mixer. Mixed stream 218 can have an oil-to-water weight (wt/wt) ratio ranging between about 1:1 and about 0.1:1 at standard temperature and pressure (SATP), alternately between about 0.7:1 and about 0.2:1 at SATP, or alternately between about 0.5:1 and about 0.2:1 at SATP. In at least one embodiment, mixed stream 218 has an oil-to-water weight ratio ranging between about 0.5:1 and about 0.2:1 at SATP.

Mixed stream 218 is introduced to reactor 114. Reactor 114 is maintained at a temperature and pressure such that the water is in its supercritical state. Reactor 114 can be maintained at a temperature ranging between about 300 deg. C. and about 550 deg. C., alternately between about 380 deg. C. and about 475 deg. C., or alternately between about 420 deg. C. and about 450 deg. C. In at least one embodiment, reactor 114 is maintained at a temperature ranging between about 420 deg. C. and about 450 deg. C. Means for maintaining such temperature of reactor 114 can include a strip heater, immersion heater, tubular furnace, heat exchanger, or like devices known in the art. Reactor 114 can be maintained at a pressure greater than about 22 MPa, alternately between about 23 MPa and about 30 MPa, or alternately between about 24 MPa and about 28 MPa. In at least one embodiment, reactor 114 is maintained at a pressure ranging between about 25 MPa and about 27 MPa. Reactor 114 can be a horizontal tubular type reactor, vertical tubular type reactor, inclined tubular type reactor, vessel type reactor, CSTR type and combinations of the same. In at least one embodiment, reactor 114 includes a tubular reactor, which advantageously prevents precipitation of reactants or products in the reactor. Reactor 114 can include an upflow reactor, a downflow reactor, and a combination of an upflow reactor and a downflow reactor. Reactor 114 can have a Reynolds number greater than about 3,000, alternately greater than about 4,000, or alternately greater than about 5,000. In at least one embodiment, reactor 114 has a Reynolds number greater than about 5,000. Maintaining such Reynolds number in reactor 114 ensures full development of turbulence in reactor 114 to prevent secondary reactions of produced LAOs. The components of mixed stream 218 can have a residence time in reactor 114 ranging between about 0.1 minute (min) and about 60 min, alternately between about 0.2 min and about 30 min, or alternately between about 0.5 min and about 10 min. The residence time is calculated by assuming that the density of the reactants is substantially identical to that of water at operating conditions of reactor 114. The residence time can be controlled such that secondary reactions of produces LAOs are prevented.

In reactor 114, the disulfide compounds undergo homolytic splitting of the disulfide (S—S) bond in supercritical water conditions to produce thiyl radicals as shown in the following reaction:

$$RCH_2—CH_2—S—S—CH_2—CH_2—R' \rightarrow RCH_2—CH_2—S\cdot + R'CH_2—CH_2—S\cdot \quad \text{Reaction (3)}$$

where R and R' each represents an alkyl group containing at least one carbon. In the absence of HDCs, the resulting homolytically split thiyl radicals can undergo rearrangement to produce LAOs as shown in the following reactions.

$$RCH_2—CH_2—S\cdot \rightarrow RCH=CH_2 + HS\cdot \quad \text{Reaction (4)}$$

$$R'CH_2—CH_2—S\cdot \rightarrow R'CH=CH_2 + HS\cdot \quad \text{Reaction (5)}$$

However, the presence of HS· radicals as wells as other hydrogen containing radicals such as the thiyl radical itself can induce secondary reactions such as double bond migration (isomerization) to produce internal olefins, cyclization to produce naphthenes, and aromatization to produce aromatics. The presence of HDCs (for example, tetralin) prevent such secondary reactions as shown in the following reaction by removing HS· radicals:

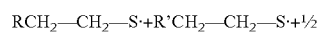

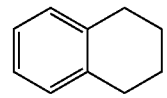

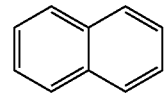

Reaction (6)

where

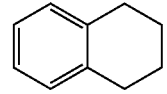

is tetralin and

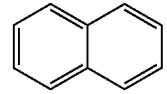

is naphthalene, which is the dehydrogenated product of tetralin. As shown in Reaction (6), a partially hydrogenated multi-ring aromatic compound such as tetralin donates hydrogen atoms and converts to its stable, fully aromatic form, naphthalene.

In at least one embodiment, reactor 114 is in the absence of an external supply of catalyst. In at least one embodiment, reactor 114 is in the absence of an external supply of hydrogen. The product of reactor 114 is collected via effluent stream 220.

Effluent stream 220 can be passed to heat exchanger 116 such that effluent stream 220 is cooled. Heat exchanger 116 can be any type of heat exchange device capable of reducing the temperature of effluent stream 220. Non-limiting examples of heat exchanger 116 can include double pipe type exchanger, shell-and-tube type exchanger, and air cooler. In some embodiments, heat exchanger 116 and heat exchanger 108 are integrated as a single heat exchanger such that effluent stream 220 can be cooled and water stream 214 can be heated. The temperature of effluent stream 220 can be reduced in heat exchanger 116 to produce effluent stream 222. The temperature of effluent stream 222 can range between about 20 deg. C. and about 350 deg. C., alternately between about 30 deg. C. and about 200 deg. C., or alternately between about 50 deg. C. and about 110 deg. C.

In at least one embodiment, the temperature of effluent stream 222 ranges between about 50 deg. C. and about 110 deg. C.

Effluent stream 222 is passed to pressure reducer 118 to produce effluent stream 224. Pressure reducer 118 can be any type of device capable of reducing the pressure of a fluid stream. Non-limiting examples of pressure reducer 118 can include a pressure let-down valve, a pressure control valve, a back pressure regulator, and a coil. Multiple pressure reducers 118 can be connected in series. In at least one embodiment, pressure reducer 118 includes two or three serially connected pressure control valves. The pressure of effluent stream 222 is reduced such that the pressure of effluent stream 222 can range between about 0.01 MPa and about 10 MPa, alternately between about 0.01 MPa and about 7 MPa, or alternately between about 0.01 MPa and about 5 MPa. In at least one embodiment, the effluent stream 224 is at about ambient pressure (that is, about 0.10 MPa). The pressure of effluent stream 224 is maintained at a pressure greater than the steam pressure of water at the temperature of effluent stream 224.

Effluent stream 224 is introduced to separator 120. Separator 120 can be any type of separation device capable of separating a fluid stream into a gas phase stream and a liquid phase stream. Effluent stream 224 is separated to produce gas stream 226 and liquid stream 228. Gas stream 226 can include gaseous products of reactor 114. Non-limiting example gaseous products include hydrogen sulfide, methane, ethane, ethylene, propane, propylene, n-butane, isobutane, α-butylene, cis-β-butylene, trans-β-butylene, and isobutylene. Liquid stream 228 can include liquid products of reactor 114. In some embodiments, liquid stream 228 can include hydrogen sulfide dissolved in the liquid products of reactor 114.

Liquid stream 228 is introduced to separator 122. Separator 122 can be any type of separation device capable of separating a liquid stream into a hydrocarbon-containing stream and a water stream. Liquid stream 228 is separated to produce hydrocarbon stream 230 and water stream 232. In some embodiments, separator 122 is operated in the absence of a demulsifying agent. In some embodiments, water stream 232 includes hydrocarbons having a density greater than that of water.

Hydrocarbon stream 230 is introduced to distillation unit 124. Distillation unit 124 includes distillation columns that are capable of separating hydrocarbon stream 230 into LAO stream 234 and byproduct stream 236. LAO stream 234 includes LAOs. Byproduct stream 236 can include organic sulfur compounds other than disulfides, unreacted and reacted HDCs, and unreacted disulfides.

Figure 3:
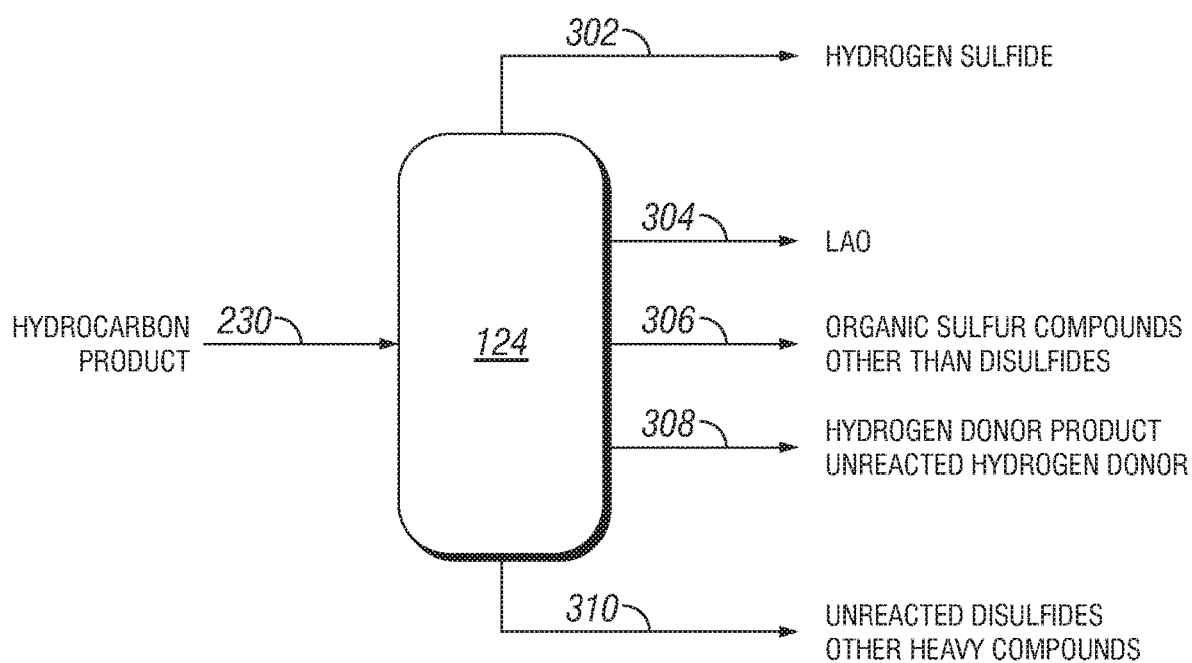
FIG. 3 is a schematic diagram of a distillation unit for LAO production according to an embodiment of the disclosure.

In an alternate embodiment, as shown in FIG. 3, distillation unit 124 can include distillation columns that are capable of separating multiple components included in hydrocarbon stream 230. An example process 100 using a disulfide oil including dipentyl disulfide and an HDC including tetralin can produce hydrocarbon stream 230 having a composition as shown in Table 1.

TABLE 1

| Products | Chemical Components | Boiling Point (deg. C.) |
|---|---|---|
| Gaseous | Hydrogen Sulfide (Previously dissolved in liquid product) | −60 |
| LAOs | 1-Pentene | 30 |
| Organic Sulfur | 1-Pentanethiol | 125 |

TABLE 1-continued

| Products | Chemical Components | Boiling Point (deg. C.) |
|---|---|---|
| Compounds Other Than Disulfides | | |
| Unreacted HDCs | Tetralin (1,2,3,4-Tetrahydronaphthalene) | 208 |
| Reacted (or Dehydrogenated) HDCs | Naphthalene | 218 |
| Unreacted Disulfides and Other Heavy Compounds | Dipentyl Disulfide (1-(Pentyldisulfanyl)Pentane) | 264 |

Accordingly, distillation unit 124 can have multiple columns to separate certain components of hydrocarbon stream 230 based on the boiling points of the components. For example, distillation unit 124 can separate hydrocarbon stream 230 having components as shown in Table 1 into hydrogen sulfide stream 302 (collected from the top of distillation unit 124), LAO stream 304 (collected via column corresponding to boiling points ranging between about 0 deg. C. and 80 deg. C.), organic sulfur stream 306 (collected via column corresponding to boiling points ranging between about 80 deg. C. and 180 deg. C.), HDC stream 308 (collected via column corresponding to boiling points ranging between about 180 deg. C. and 240 deg. C.), and disulfide stream 310 (collected from bottom of distillation unit 124). One skilled in the relevant art would recognize that the boiling point ranges of the columns are not fixed but can be adjusted to different ranges.

In some embodiments, HDC stream 308 includes unreacted HDCs and reacted HDCs. Reacted HDCs such as naphthalene (or in some embodiments, 1,2-dihydronaphthalene, which is a partially dehydrogenated product of tetralin) can be regenerated via catalytic partial hydrogenation to produce tetralin. Non-limiting example catalysts used for regeneration of dehydrogenated HDCs include platinum-alumina catalysts and nickel-based catalysts.

In some embodiments, disulfide stream 310 can be recycled to the process 100 via disulfide oil feed 202.

EXAMPLE

The disclosure is illustrated by the following examples, which are presented for illustrative purposes only, and are not intended as limiting the scope of the invention which is defined by the appended claims.

Example

An experiment was conducted using a laboratory scale unit with a process similar to that shown in FIG. 1. A disulfide oil feed (stream 202) was prepared by mixing dipentyl disulfide and toluene. A hydrogen donor feed (stream 204) was prepared. The hydrogen donor feed included tetralin. The disulfide oil feed and the hydrogen donor feed were combined using a tee fitting (stream 208). The mixed stream had a composition as shown in Table 2.

TABLE 2

| | Fraction (wt. %) |
|---|---|
| Dipentyl Disulfide | 31.8 |
| Tetralin | 4.0 |
| Toluene | 64.2 |

The mixed stream was pumped using a syringe pump at a mass flow rate of about 176 grams per hour (g/hr) (stream 210) and subsequently heated by a tubular furnace to a temperature of about 125 deg. C. (stream 212).

A water feed (stream 206) was prepared. The water included in the water feed was produced by a laboratory scale water purification unit. The water included in the water feed had properties compliant to ASTM type I grade. The water feed was pumped using a syringe pump at a mass flow rate of about 426 g/hr (stream 214) and subsequently heated by a tubular furnace to a temperature of about 510 deg. C. (stream 216).

The mixed stream and the water feed were combined using a tee fitting (stream 218). The mixed stream was introduced to a tubular reactor (reactor 114) made of 316L stainless steel tubing. The inner diameter of the tubing was 0.083 inch. The outer diameter of the tubing was 0.25 inch. The length of the tubing was 12.6 meters. The tubing was arranged in a helical configuration such that the diameter of the tubular reactor was about 50 centimeters. The direction of the flow was downward. The helical tubing was placed in a box furnace. The box furnace was controlled in a manner such that the temperature of the effluent was maintained at about 446 deg. C. The residence time of the reactants in the tubular reactor was calculated to be about 0.5 min. The Reynolds number of the helically configured tubular reactor was about 3,300.

The effluent (stream 220) was cooled using a double-tube type cooler to a temperature of about 45 deg. C. (stream 222) where cold water was flowing on the exterior of the cooler. The cooled stream was depressurized using a back pressure regulator to ambient pressure (stream 224). The depressurized stream was collected in a bottle equipped with a condenser to capture light hydrocarbons. Water (stream 232) was separated from the bottle.

The experiment was run for about one hour, where the resulting hydrocarbon product (stream 230) collected via the bottle contained about 12.7 grams of 1-pentene and about 32.3 grams of dipentyl disulfide. For about one hour, about 56.0 grams (=176 g/hr×31.8%) of dipentyl disulfide was introduced to the process. The conversion rate of dipentyl disulfide was about 42.3% (=1−(32.3/56.0)). The theoretical amount of 1-pentene produced at a 42.3% conversion rate was about 16.1 grams (=2×70.1×(56.0−32.3)/206.4). The calculated yield was about 82% (=12.7/16.1).

Comparative Example

A control experiment was conducted similar to Example but in the absence of the hydrogen donor feed. The calculated yield was less than about 60%. The control experiment produced other byproducts such as 1-pentanethiol, isomerized paraffins, and other high molecular weight compounds (for example, coke or asphaltenes). These byproducts were believed to be produced from inter-radical reactions or secondary reactions due to the presence of HS. radicals as wells as other hydrogen containing radicals such as the thiyl radical.

The results show that the addition of HDCs enhances the yield of LAOs by decomposing disulfide oil in the presence of supercritical water.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method for producing a linear alpha olefin (LAO), the method comprising the steps of:
    combining a disulfide oil feed and a hydrogen donor feed to produce a first mixed stream, the disulfide oil feed comprising a disulfide, the hydrogen donor feed comprising a hydrogen donating compound (HDC);
    combining the first mixed stream and a water feed to produce a second mixed stream;
    introducing the second mixed stream to a reactor, wherein the reactor is operated at a pressure equal to or greater than 22.06 MPa and a temperature equal to or greater than 373.9 deg. C. to produce an effluent stream, the effluent stream comprising the LAO;
    introducing the effluent stream to a first separator to produce a gas stream and a liquid stream, the liquid stream comprising the LAO;
    introducing the liquid stream to a second separator to produce a hydrocarbon stream and a water stream, the hydrocarbon stream comprising the LAO; and
    introducing the hydrocarbon stream to a distillation unit to produce an LAO stream and a byproduct stream, the LAO stream comprising the LAO.

2. The method of claim 1, further comprising the step of: pressurizing the first mixed stream to a pressure equal to or greater than 22.06 MPa.

3. The method of claim 1, further comprising the step of: heating the first mixed stream to a temperature ranging between 80 deg. C. and 150 deg. C.

4. The method of claim 1, further comprising the step of: pressurizing the water feed to a pressure equal to or greater than 22.06 MPa.

5. The method of claim 1, further comprising the step of: heating the water feed to a temperature ranging between 374 deg. C. and 500 deg. C.

6. The method of claim 1, further comprising the step of: cooling the effluent stream to a temperature ranging between 50 deg. C. and about 110 deg. C.

7. The method of claim 1, further comprising the step of: depressurizing the effluent stream to ambient pressure.

8. The method of claim 1, wherein the disulfide is a compound of formula (I):

R—S—S—R'  (I)

wherein R is a first alkyl group having carbon atoms ranging from 1 to 12,
wherein R' is a second alkyl group having carbon atoms ranging from 5 to 12.

9. The method of claim 8, wherein the disulfide comprises 1-(pentyldisulfanyl)pentane.

10. The method of claim 1, wherein the HDC comprises a partially hydrogenated multi-ring aromatic compound.

11. The method of claim 10, wherein the HDC is selected from the group consisting of: 1,2,3,4-tetrahydronaphthalene, 6-butyl-1,2,3,4-tetrahydronaphthalene, 7-ethyl-1,2,3,4-tetrahydronaphthalene, 9,10-dihydroanthracene, 9,10-dihydrophenanthrene, and combinations of the same.

12. The method of claim 1, wherein the first mixed stream has an HDC-to-disulfide mole ratio ranging between 0.1:1 and 0.5:1.

13. The method of claim 1, wherein the second mixed stream has an oil-to-water volume ratio ranging between 0.5:1 and 0.2:1 at standard temperature and pressure.

14. The method of claim 1, wherein the reactor is operated such that components of the second mixed stream have a residence time ranging between 0.5 minutes and 10 minutes.

15. The method of claim 1, wherein the byproduct stream comprises a dehydrogenated form of the HDC selected from the group consisting of: naphthalene, 1,2-dihydronaphthalene, anthracene, phenanthrene, and combinations of the same.

16. The method of claim 15, further comprising the step of:
regenerating the dehydrogenated form of the HDC.

17. A method for producing a linear alpha olefin (LAO), the method comprising the steps of:
combining a disulfide, a hydrogen donating compound (HDC), and water to produce a mixture; and
pressurizing the mixture to a pressure equal to or greater than 22.06 MPa and heating the mixture to a temperature equal to or greater than 374 deg. C. to produce an effluent stream comprising the LAO,
wherein the disulfide is a compound of formula (I):

R—S—S—R'  (I)

wherein R is a first alkyl group having carbon atoms ranging from 1 to 12,
wherein R' is a second alkyl group having carbon atoms ranging from 5 to 12,
wherein the HDC comprises a partially hydrogenated multi-ring aromatic compound.

18. The method of claim 17, wherein the disulfide comprises 1-(pentyldisulfanyl)pentane.

19. The method of claim 17, wherein the HDC is selected from the group consisting of: 1,2,3,4-tetrahydronaphthalene, 6-butyl-1,2,3,4-tetrahydronaphthalene, 7-ethyl-1,2,3,4-tetrahydronaphthalene, 9,10-dihydroanthracene, 9,10-dihydrophenanthrene, and combinations of the same.

20. A system for producing a linear alpha olefin (LAO), the system comprising:
a first mixer, the first mixer configured to combine a disulfide oil feed and a hydrogen donor feed to produce a first mixed stream, wherein the disulfide oil feed comprises a disulfide, the hydrogen donor feed comprises a hydrogen donating compound (HDC);
a first pump, the first pump fluidly connected downstream of the first mixer, the first pump configured to pressurize the first mixed stream to a pressure equal to or greater than 22.06 MPa;
a first heat exchanger, the first heat exchanger fluidly connected downstream of the first mixer, the first heat exchanger configured to heat the first mixed stream to a temperature ranging between 80 deg. C. and 150 deg. C.;
a second pump, the second pump configured to pressurize a water feed to a pressure equal to or greater than 22.06 MPa;
a second heat exchanger, the second heat exchanger configured to heat the water feed to a temperature ranging between 374 deg. C. and 500 deg. C.;
a second mixer, the second mixer fluidly connected downstream of the first pump and the first heat exchanger and fluidly connected downstream of the second pump and the second heat exchanger, the second mixer configured to combine the first mixed stream and the water feed to produce a second mixed stream;
a reactor, the reactor fluidly connected downstream of the second mixer, the reactor operated at a pressure equal to or greater than 22.06 MPa and a temperature equal to or greater than 373.9 deg. C. to produce an effluent stream, wherein the effluent stream comprises the LAO;
a third heat exchanger, the third heat exchanger fluidly connected downstream of the reactor, the third heat exchanger configured to cool the effluent stream to a temperature ranging between 50 deg. C. and about 110 deg. C.;
a pressure reducer, the pressure reducer fluidly connected downstream of the reactor, the pressure reducer configured to depressurize the effluent stream to ambient pressure;
a first separator, the first separator fluidly connected downstream of the third heat exchanger and the pressure reducer, the first separator configured to separate the effluent stream into a gas stream and a liquid stream, wherein the liquid stream comprises the LAO;
a second separator, the second separator fluidly connected downstream of the first separator, the second separator configured to separate the liquid stream into a hydrocarbon stream and a water stream, wherein the hydrocarbon stream comprises the LAO; and
a distillation unit, the distillation unit fluidly connected downstream of the second separator, the distillation unit configured to separate the hydrocarbon stream to produce an LAO stream and a byproduct stream, wherein the LAO stream comprises the LAO.

21. The system of claim 20, further comprising:
a Merox unit, the Merox unit fluidly connected upstream of the first mixer, the Merox unit configured to produce the disulfide oil feed by removing sulfur from naphtha and kerosene.

* * * * *